US012678418B2

(12) United States Patent
Szewczuk et al.

(10) Patent No.: US 12,678,418 B2
(45) Date of Patent: Jul. 14, 2026

(54) COMPOSITIONS AND METHODS FOR THE TREATMENT OF THREATENED RESPIRATORY FAILURE CAUSED BY CORONAVIRUS INFECTION AND DISEASE

(71) Applicants: ENCYT TECHNOLOGIES, INC., Membertou (CA); Myron R. Szewczuk, Kingston (CA)

(72) Inventors: Myron R. Szewczuk, Kingston (CA); William Warren Harless, Black Rock (CA)

(73) Assignees: ENCYT TECHNOLOGIES, INC., Membertou (CA); Myron R. Szewczuk, Kingston (CA)

(*) Notice: Subject to any disclaimer, the term of this patent is extended or adjusted under 35 U.S.C. 154(b) by 796 days.

(21) Appl. No.: 17/912,711

(22) PCT Filed: Mar. 18, 2021

(86) PCT No.: PCT/CA2021/050362
§ 371 (c)(1),
(2) Date: Sep. 19, 2022

(87) PCT Pub. No.: WO2021/184123
PCT Pub. Date: Sep. 23, 2021

(65) Prior Publication Data
US 2023/0172888 A1 Jun. 8, 2023

Related U.S. Application Data

(60) Provisional application No. 62/991,387, filed on Mar. 18, 2020.

(51) Int. Cl.
*A61K 31/215* (2006.01)
*A61K 9/00* (2006.01)
(Continued)

(52) U.S. Cl.
CPC .......... *A61K 31/215* (2013.01); *A61K 9/0073* (2013.01); *A61K 31/616* (2013.01); *A61P 31/14* (2018.01)

(58) Field of Classification Search
CPC .. A61K 2300/00; A61K 31/18; A61K 31/215; A61K 31/351; A61K 31/4985;
(Continued)

(56) References Cited

U.S. PATENT DOCUMENTS 10,350,188 B2 7/2019 Szewczuk

FOREIGN PATENT DOCUMENTS

CA 2527711 A1 12/2004
CN 111991401 A 11/2020
(Continued)

OTHER PUBLICATIONS

Jianlei, L, et al, Effect of aspirin on reducing the incidence of ARDS: a meta-analysis, Clinical Focus, Jun. 20, 2019, vol. 34, No. 6. (Translation).

(Continued)

*Primary Examiner* — Savitha M Rao
(74) *Attorney, Agent, or Firm* — Norton Rose Fulbright Canada LLP

(57) ABSTRACT

A method of treating a coronavirus infection involves administering an inhibitor of the Neu1 sialidase-G protein-coupled receptor-Matrix metalloproteinase 9 (Neu1-GPCR-MMP9) signaling platform, in particular administering intravenously or by inhalation to a patient infected with COVID-19 and its variants a therapeutically effective amount of oseltamivir phosphate, preferably in conjunction with the oral administration of aspirin, in order to reduce the symptoms of respiratory compromise and/or prevent Acute Respiratory Distress Syndrome (ARDS).

17 Claims, 9 Drawing Sheets

(51) Int. Cl.
*A61K 31/616* (2006.01)
*A61P 31/14* (2006.01)

(58) Field of Classification Search
CPC .............. A61K 31/616; A61K 31/7012; A61K 9/0073; A61P 31/14
See application file for complete search history.

(56) References Cited

FOREIGN PATENT DOCUMENTS

| | | | |
|---|---|---|---|
| EP | 2773340 | B1 | 1/2020 |
| WO | 2005056047 | A1 | 6/2005 |
| WO | 2009137916 | A1 | 11/2009 |
| WO | 2011047466 | A1 | 4/2011 |
| WO | 2011076367 | A2 | 6/2011 |
| WO | 2013063679 | A1 | 5/2013 |

OTHER PUBLICATIONS

Machine Translation Version of CN 111991401 A.
Zhu, N., et al. (2020). A Novel Coronavirus from Patients with Pneumonia in China, 2019. N Engl J Med. 382, 727-733.
Fujishima, S. Pathophysiology and biomarkers of acute respiratory distress syndrome. j intensive care 2, 32 (2014).
Li, W et al. Angiotensin-converting enzyme 2 is a functional receptor for the SARS coronavirus. Nature 426, 450-454 (2003).
Leonhardt, Julia et al. Evidence for Heterodimerization and Functional Interaction of the Angiotensin Type 2 Receptor and the Receptor MAS Hypertension. 2017;69:1128-1135.
Amith, Jayanth et al. (2009) Glycoconj J 26 p. 1197-1212.
Abdulkhalek, Guo et al. Cellular Signalling 24 (2012) 2035-2042.
Baranovich, T et al, The Neuraminidase Inhibitor Oseltamivir Is Effective Against A/Anhui/1/2013 (H7N9) Influenza Virus in a Mouse Model of Acute Respiratory Distress Syndrome, The Journal of Infectious Diseases 2014;209:1343-1353.
Brennan, B, et al, Safety, Tolerability, and Pharmacokinetics of Intravenous Oseltamivir: Single- and Multiple-Dose Phase I Studies with Healthy Volunteers, Antimicrobial Agents and Chemotherapy, Sep. 2012 vol. 56 No. 9 p. 4729-4737.
Guo, L et al, Long-term outcomes in patients with severe acute respiratory syndrome treated with oseltamivir: a 12-year longitudinal study, Int J Clin Exp Med 2019; 12(10):12464-12471.
Ju, T et al, Golden Hour For Administering Oseltamivir in Severe Influenza Complicating Adrs? A Multicenter Retrospective Study, CHEST Annual Meeting, 2018, American College of Chest Physicians. Published by Elsevier Inc.
Lai, C et al., Severe acute respiratory syndrome coronavirus 2 (SARS-COV-2) and coronavirus disease-2019 (COVID-19): The epidemic and the challenges, International Journal of Antimicrobial Agents 55 (2020) 105924.
Leyva-Grado, V et al, Aerosol administration increases the efficacy of oseltamivir for the treatment of mice infected with influenza viruses, Antiviral Research 142 (2017) 12-15.
Lu, H, Drug treatment options for the 2019-new coronavirus (2019-nCo V), BioScience Trends. 2020; 14(1):69-71.
Munir, M et al, The Efficacy and Safety of Antivirus Drugs for COVID-19: A Systematic Review, Sys Rev Pharm 2020;11{7): 162-166.
Panka, B et al, Prevention or treatment of ARDS with aspirin: a review of preclinical models and meta-analysis of clinical studies, Shock. Jan. 2017; 47(1): 13-21.
CA Examiner's Requisition, CA 3175927, Canadian Intellectual Property Office, Jan. 3, 2024.
EP Search Report & Opinion, EP 21 77 1275, European Patent Office, Feb. 19, 2024.

FIB. 3C

COMPOSITIONS AND METHODS FOR THE TREATMENT OF THREATENED RESPIRATORY FAILURE CAUSED BY CORONAVIRUS INFECTION AND DISEASE

This application claims priority to U.S. provisional patent application 62/991,387 filed Mar. 18, 2020.

TECHNICAL FIELD

This disclosure generally relates to the field of treatments for coronavirus infections.

BACKGROUND OF THE ART

In December 2019, an enveloped single stranded positive RNA virus was identified as the causal agent for a cluster of potentially fatal pneumonias that were first identified in Wuhan, China. This novel corona virus (COVID-19) was termed severe acute respiratory syndrome (SARS)-CoV-2, and was found to be similar to the corona virus that was responsible for the SARS pandemic that occurred in 2002. (Zhu, N., et al. (2020). A Novel Coronavirus from Patients with Pneumonia in China, 2019. N Engl J Med. 382, 727-733).

The manifestations of COVID-19 infection can vary across a broad range of clinical manifestations. Patients can be asymptomatic while shedding the virus, experience mild upper respiratory tract infection, or symptomatic and potentially life-threatening pneumonia with Acute Respiratory Distress Syndrome (ARDS) and multisystem organ failure.

Since the outbreak of cases in China in December 2019 and the rapid spread of the disease worldwide, the COVID-19 virus has emerged as a global pandemic with significant threat to human life. Death from infection with this virus is typically associated with acute respiratory failure, most notably ARDS. Individuals with premorbid conditions, including heart disease, diabetes, and smokers appear to be at greater risk for mortality from infection with this virus.

The pathophysiologic process known as ARDS is associated with an inflammatory response that ultimately leads to fluid within the alveoli leading to respiratory failure. ARDS is defined as an acute-onset, progressive, hypoxic condition with radiographic bilateral lung infiltration that can develop from several different disease processes or injuries and not from hydrostatic pulmonary edema (Fujishima, S. Pathophysiology and biomarkers of acute respiratory distress syndrome. *j intensive care* 2, 32 (2014).)

ARDS is associated with an inflammatory cascade that ultimately leads to respiratory failure and pulmonary edema. Increased vascular permeability within the lung tissues leads to pulmonary edema and the clinical consequence of respiratory failure. The increase in vascular permeability can be due to a number of factors including tissue injury and multiple inflammatory cascades. Uncontrolled inflammatory cascades are critical to the pathophysiology of the clinical syndrome of ARDS.

There is an urgent need for novel treatments for coronavirus infections and, in particular, for the treatment and prevention of ARDS associated with coronavirus infection, especially COVID-19.

Another condition associated with an uncontrolled inflammatory cascade and frequently ARDS is sepsis. Sepsis is a common cause of hospitalizations and deaths among hospitalized patients. There is a need for novel treatments for sepsis patients, including those at risk of developing ARDS.

SUMMARY OF THE INVENTION

In one embodiment, there is provided a method of treating a coronavirus infection or a suspected coronavirus infection comprising administering to a subject in need thereof a therapeutically effective amount of an inhibitor of the Neu1 sialidase-G protein-coupled receptor-Matrix metalloproteinase 9 (Neu1-GPCR-MMP9) signaling platform to inhibitACE2 activation by desialylation by activated Neu1.

In some embodiments, the inhibitor of the Neu1-GPCR-MMP9 signaling platform is a Neu1 sialidase inhibitor, preferably oseltamivir phosphate (OP) or an analogue thereof or 2-deoxy-2,3-dehydro-N-acetylneuraminic acid (DANA) or an analogue thereof, an inhibitor of MMP-9 or an inhibitor of the heterotrimeric G-protein complex.

In some embodiments, administering the inhibitor of the Neu1-GPCR-MMP9 signaling platform decreases the plasma/serum level of one or more of IL-6, TNFα, and/or G-CSF pro-inflammatory cytokines within 24 hours, preferably a decrease of ≥5%, ≥10% or ≥25% within 24 hours and/or administering the inhibitor of the Neu1-GPCR-MMP9 signaling platform decreases viral load within 24 hours, preferably a decrease of ≥5%, ≥10% or ≥25% within 24 hours.

Also provided is a method of treating a coronavirus infection or suspected coronavirus infection comprising administering intravenously or via inhalation to a subject in need thereof a therapeutically effective amount of OP or an analogue thereof.

Also provided is a method of treating or preventing ARDS comprising administering intravenously or via inhalation to a subject in need thereof a therapeutically effective amount of oseltamivir phosphate or an analogue thereof. The subject may be diagnosed with a coronavirus infection and/or with sepsis.

In any of the above methods, the coronavirus may be COVID-19 or a variant thereof.

In one embodiment, the method comprises administering a therapeutically effective amount of OP intravenously or via inhalation.

In the disclosed methods or uses, the subject may have atelectasis and/or hypoxemia.

The subject may have one or more symptoms of respiratory compromise selected from shortness of breath, rapid breathing, and bluish skin coloration and the method or use can ameliorate or alleviate one or more of these symptoms.

In one embodiment, the method comprises administering OP or an analogue thereof at a daily dose of between 100 mg and 1000 mg.

The method may further include administering a therapeutically effective amount of aspirin to the subject, which in one embodiment, may be administered orally concurrently with the OP, in one embodiment, at a daily dose of between 100 mg and 1000 mg.

Also provide is use or use in the manufacture of a medicament of an inhibitor of the Neu1-GPCR-MMP9 signaling platform to inhibit ACE2 desialylation process by activated Neu1 for the treatment of a coronavirus infection or a suspected coronavirus infection. In some embodiments, the inhibitor of the Neu1-GPCR-MMP9 signaling platform is a Neu1 sialidase inhibitor, preferably OP or an analogue thereof or DANA or an analogue thereof, an inhibitor of MMP-9 or an inhibitor of the heterotrimeric G-protein complex.

In some embodiments, administration of the inhibitor of the Neu1-GPCR-MMP9 signaling platform decreases the plasma/serum level of one or more of IL-6, TNFα, and/or G-CSF pro-inflammatory cytokines within 24 hours, preferably a decrease of ≥5%, ≥10% or ≥25% within 24 hours and/or administration of the inhibitor of the Neu1-GPCR-MMP9 signaling platform decreases viral load within 24 hours, preferably a decrease of ≥5%, ≥10% or ≥25% within 24 hours.

Also, provided is use or use in the manufacture of a medicament of a therapeutically effective amount of OP or an analogue thereof administered intravenously or via inhalation for the treatment of a coronavirus infection or suspected coronavirus infection.

Also provided is use or use in the manufacture of a medicament of a therapeutically effective amount of OP or an analogue thereof administered intravenously or via inhalation for the treatment or prevention ARDS. The subject may be diagnosed with a coronavirus COVID-19 or a variant infection and/or with sepsis.

In any of the above uses, the coronavirus may be COVID-19 or a variant thereof.

The inhibitor of the Neu1-GPCR-MMP9 signaling platform may be used in combination with aspirin. In one embodiment, aspirin is administered orally concurrently with OP. Aspirin may be used at a daily dose of between 100 mg and 1000 mg.

In one embodiment, there is provided a treatment regimen comprising: administering to the subject a bolus dose of between 150 mg and 250 mg of OP by intravenous injection; subsequently administering an additional dose of between 150 mg and 250 mg of OP over 24 hours by continuous infusion; and orally administering to the subject aspirin at a dose of between 450 mg and 550 mg.

Also provided is a pharmaceutical aerosol formulation comprising particles of OP dispersed in a propellant.

BRIEF DESCRIPTION OF THE DRAWINGS

FIG. 3C shows sialidase activity in live RAW-blue macrophage cells associated with angiotensin 1-7 at various concentrations as determined by a SEAP reporter assay per Example 2. Angiotensin 1-7 triggered increased expression of SEAP, which is reflective of NF-kB expression and downstream induction of inflammatory molecules.

DETAILED DESCRIPTION

Figure 1:
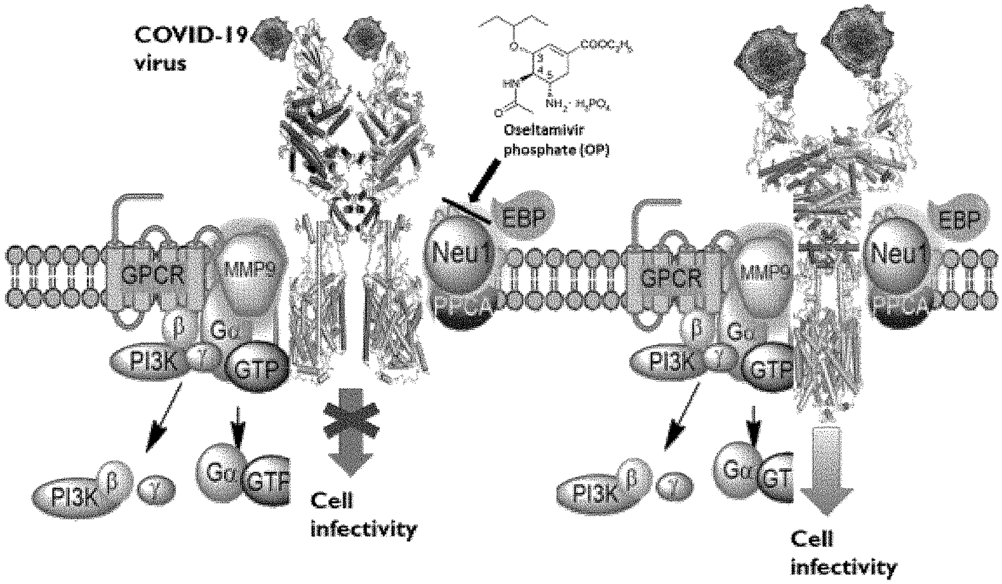
FIG. 1 shows a graphical ACE2 model. COVID-19 S-protein potentiates the G protein coupled receptor (GPCR) signaling and Matrix metalloproteinase 9 (MMP-9) activation to induce Neu1 sialidase. Activated MMP-9 removes the elastin-binding protein (EBP) as part of the molecular multi enzymatic complex that contains β-galactosidase/Neu1 and protective protein cathepsin A (PPCA). Activated Neu1 hydrolyzes α-2,3 sialyl residues of ACE2 at the protease domain (PD) to remove steric hindrance to facilitate ACE2 subunits association to become activated. Oseltamivir phosphate (OP) specifically targets Neu1 and prevents ACE2 subunits association following COVID-19 S-protein binding. Abbreviations: Pi3K, phosphatidylinositol 3-kinase; GTP, guanine triphosphate.

In one embodiment, there is provided a novel therapeutic strategy for treating or preventing coronavirus infections comprising administering to a patient an inhibitor of the novel Neu1 sialidase-G protein-coupled receptor-Matrix metalloproteinase 9 (Neu1-GPCR-MMP9) signaling platform described further below.

In one embodiment, a patient is treated with oseltamivir phosphate (OP) administered intravenously or via inhalation. In one embodiment the OP is administered in combination with aspirin.

The novel therapeutic strategies provided herein may be administered to patients diagnosed with or suspected of having a COVID-19 virus infection and, in particular, patients exhibiting clinical signs suggestive of respiratory compromise.

In one embodiment, there is provided a method of treating a patient at risk of ARDS. In one embodiment, there is provided a method of treating a patient with sepsis that is at risk of ARDS.

As used herein "subject" refers to an organism being treated, in one embodiment a mammal, preferably a human patient.

As used herein, "therapeutically effective amount" refers to an amount effective, at dosages and for a particular period of time necessary, to achieve the desired therapeutic result.

A therapeutically effective amount of the pharmacological agent may vary according to factors such as the disease state, age, sex, and weight of the individual, and the ability of the pharmacological agent to elicit a desired response in the individual.

As used herein, "treatment" means a medical intervention for obtaining beneficial or desired results, including clinical results. Beneficial or desired results can include alleviating or ameliorating one or more symptoms or conditions, diminishing the extent of disease, stabilizing (i.e. not worsening) state of disease, or delaying or slowing disease progression. Treatment may also be preventative. The treatment may require administration of multiple doses at regular intervals or prior to onset of a disease or condition to alter the course of the disease or condition.

Coronaviruses

Coronaviruses, including COVID-19, infect human cells using the SARSCoV-2 spike (S) glycoprotein. 2 spike (S) glycoprotein binds to the cell membrane protein angiotensin-converting enzyme 2 (ACE2) to enter human cells (Li, W et al. Angiotensin-converting enzyme 2 is a functional receptor for the SARS coronavirus. *Nature* 426, 450-454 (2003).) COVID-19 has been shown to bind to ACE2 via the S glycoprotein on its surface to enter human cells. During the infection, the S glycoprotein is cleaved into subunits, S1 and S2. S1 contains the receptor binding domain (RBD) which allows coronaviruses to directly bind to the peptidase domain (PD) of ACE2. S2 plays a role in membrane fusion. ACE2 needs to dimerize to be active. The resultant homodimer has two PDs, able to bind two COVID-19 S protein trimers simultaneously. COVID-19 S proteins form trimers with two of the RBDs facing one direction (down) and the other facing the opposite way (up).

The ligand(s) trigger for the dimerization of the ACE 2 receptor and subsequent permissive state allowing for viral entry into the cell via S protein binding continue to be investigated. Ligand independent dimerization for the cell surface ACE 2 receptor is considered likely as well (*Julia* Leonhardt et al. *Evidence for Heterodimerization and Functional Interaction of the Angiotensin Type* 2 *Receptor and the Receptor* MAS Hypertension. 2017; 69:1128-1135). Steric hindrance from glycosylated residues interferes with dimerization of the ACE 2 surface receptor.

ACE2 is expressed predominantly in vascular endothelial cells of the heart and kidney. Whereas ACE converts angiotensin I to angiotensin 11, which has 8 amino acids, ACE2 converts angiotensin I to angiotensin 1-9, which has 9 amino acids. Whereas angiotensin II is a potent blood vessel constrictor, angiotensin 1-9 has no effect on blood vessels but can be converted by ACE to a shorter peptide, angiotensin 1-7, which is a blood vessel dilator.

Spike (S) proteins of coronaviruses, including the coronavirus that causes severe acute respiratory syndrome (SARS), associate with cellular receptors to mediate infection of their target cells. Li et al. Nature. 2003 Nov. 27; 426(6965):450-4) identified ACE2, isolated from SARS coronavirus-permissive Vero E6 cells, that efficiently binds the S1 domain of the SARS coronavirus S protein. Li et al. (2003) found that a soluble form of ACE2, but not of the related enzyme ACE1, blocked association of the S1 domain with Vero E6 cells. 293T cells transfected with ACE2, but not those transfected with HIV-1 receptors, formed multinucleated syncytia with cells expressing S protein. Furthermore, SARS coronavirus replicated efficiently on ACE2-transfected but not mock-transfected 293T cells. Finally, anti-ACE2 but not anti-ACE1 antibody blocked viral replication on Vero E6 cells. Li et al. (2003) concluded that ACE2 is a functional receptor for SARS coronavirus.

The finding that SARS-CoV-2 and SARS-CoV use the ACE2 receptor for cell entry has important implications for understanding SARS-CoV-2 transmissibility and pathogenesis. SARS-CoV and, presumptively, SARS-CoV-2 lead to downregulation of the ACE2 receptor, but not ACE, through binding of the spike protein with ACE2. This leads to viral entry and replication, as well as severe lung injury.

Multiple SARS-CoV-2 variants are circulating globally, including variants that have emerged in the UK (known as 201/501Y.V1, VOC 202012/01, or B.1.1.7), in South Africa, (known as 20H/501Y.V2 or B.1.351) and Brazil, (known as P.1). Variants may be associated not only with increased transmissibility and severity of disease, but also with decreased vaccine effectiveness, reinforcing the need for novel coronavirus treatments.

In January 2021, scientists from UK reported evidence that suggests the B.1.1.7 variant may be associated with an increased risk of death compared with other variants. This variant has a mutation in the receptor binding domain (RBD) of the spike protein (S-protein) at position 501, where the amino acid asparagine (N) has been replaced with tyrosine (Y). The shorthand for this mutation is N501Y. This variant also has several other mutations, including 69/70 deletion, which has occurred spontaneously many times and likely leads to a conformational change in the spike protein; and P681H near the S1/S2 furin cleavage site, a site with high variability in coronaviruses, and which mutation has also emerged spontaneously multiple times; and SARS2-S D614G (spike aspartic acid-614 to glycine). The SARS2-S D614G variant displays highest entry efficiency among natural S variants. The D614G variant is believed to have increased the ability of the virus to be transmitted and is now the most common type circulating in the UK. The D614G mutation confers structural flexibility to S protein and D614G protein binds ACE2 more efficiently than WT protein. SARS-CoV-2 D614G spike mutation increases entry efficiency with enhanced ACE2-binding affinity. As detailed further in the Examples, the present inventors provide evidence that composition and methods of the present invention will be effective in the treatment of infections caused by both the originally identified SARV-Cov-2 and its variants, including those with mutations leading to conformational changes in the spike protein such as B.1.1.7.

Activation of TLRs

Toll-like Receptor (TLR) family members play a vital role in the innate and adaptive immune response and are activated in COVID-19 infection. These receptors upregulate pro-inflammatory mediators such as IL-6 through the activation of nuclear factor kappa B (NF-kB). Inflammatory stimuli, such as endotoxin LPS or a virus, can trigger TLR dimerization and downstream signaling either by directly binding to the TLR or through a transactivation process ligand binding to G protein-coupled receptors. When a virus or inflammatory stimulus binds to the TLR, it induces a conformational change in the TLR, which triggers activation of the G-protein coupled receptor (GPCR). This GPCR activation will then trigger the activation of MMP-9, which cleaves the elastin binding protein (EBP) tethered to Neu-1. This process involves the EBP as part of the molecular multi enzymatic complex that contains β-galactosidase/Neu1 and protective protein cathepsin A (PPCA). Direct removal of EBP from the complex by activated MMP-9 may activate Neu1. Alternatively, binding of elastin fragments to EBP may induce activation of Neu1 by EBP dissociation. Activated Neu1 hydrolyzes α-2,3-sialic acid residues of the glycosylated TLR receptors at the ectodomain to remove steric hindrance and facilitate receptor association and activation. This process is critical to understanding the predicted role of Neu-1 in the pathophysiology of SARS viruses. Evidence is provided that Neu-1 is involved in both Toll-like receptor dimerization and activation induced by Neu 1 as well as ACE-2 receptor dimerization and activation, permitting viral entry into the cell.

While NEU-1 plays a critical role in the inflammatory response via its role in permitting the TLR to dimerize and downstream signaling, the inventors further provide evidence that a virtually identical signaling cascade is involved with COVID-19 infection and entry into the host cell via the ACE-2 receptor.

In particular, with reference to FIG. 1, COVID-19 S-protein potentiates the GPCR-signaling and MMP-9 activation to induce Neu1 sialidase. Activated MMP-9 removes EBP as part of the molecular multi enzymatic complex that contains β-galactosidase/Neu1 and PPCA. Activated Neu1 hydrolyzes α-2,3 sialyl residues of ACE2 at the protease domain (PD) to remove steric hindrance to facilitate ACE2 subunits association to become activated.

ACE2 is a specific functional receptor for SARS-CoV2. The ACE2 receptor must dimerize to be permissive for viral internalization into the cell. There is evidence that a requisite desialylation process initiated by NEU-1 plays a pivotal role in permitting receptor dimerization and, therefore, viral entry into the cell, providing novel treatment options as detailed further below.

As detailed in the Examples, using a Secreted Embryonic Alkaline Phosphatase (SEAP) reporter assay this signaling pathway was determined to be activated by various agonists of G protein receptors and the level of expression of SEAP in response to inflammatory stimuli such as endotoxin lipopolysaccharide (LPS) recombinant and S protein—the molecule used by the COVID-19 virus to internalize into the cell via the ACE-2 receptors—was studied. SEAP in this context reflects the level of expression of NF-kB, which is responsible for inducing IL-6 and therefore reflective of receptor activation.

Thus, coronavirus treatments provided herein can be associated with both a decrease in viral load (as a consequence of inhibition of viral internationalization into the cell) and a decrease in markers of inflammation. Without limiting the generality of the foregoing, cytokines associated with coronarivus and, in particular, COVID-19 infection and an inflammatory cascade are further identified below and, in particular embodiments, may be one or more of IL-6, TNFα, and/or G-CSF. Methods of measuring coronavirus infection viral load and cytokine levels in patient plasma/serum are known to those of skill in the art. In some embodiments, administration of treatments provided herein is associated with an observable decrease in both viral load and marker of inflammation within 24 hours, in various embodiments, a decrease of ≥5%, ≥10% or ≥25%.

Given commonalities in structure and mechanism of infection, the disclosed treatments associated with the Neu1 sialidase-G protein-coupled receptor-Matrix metalloproteinase 9 (Neu1-GPCR-MMP9) signaling platform will be applicable not only to COVID-19 and variants thereof, but to other coronaviruses.

Inhibiting Viral Entry Via Neu1 Sialidase-G Protein-Coupled Receptor-Matrix Metalloproteinase 9 (Neu1-GPCR-MMP9) Signaling Pathway Thus, in one embodiment, there is provided a method of inhibiting cellular internalization of a coronavirus and, in particular, COVID-19, thereby reducing infectivity and viral load comprising administering to a patient an inhibitor of the Neu1 sialidase-G protein-coupled receptor-Matrix metalloproteinase 9 (Neu1-GPCR-MMP9) signaling platform described above.

In one embodiment, the inhibitor is a MMP9 inhibitor. In some embodiments, the MMP9 inhibitor may be selected from the following list:

- Galardin (GM6001; Calbiochem-EMD Chemicals Inc., Darmstadt, Germany) is a potent, cell-permeable, broad-spectrum hydroxamic acid inhibitor of matrix metalloproteinases (MMPs) (IC50=400 pM for MMP1; IC50=500 pM for MMP2; IC50=27 nM for MMP3; IC50=100 pM for MMP8; and IC50=200 pM for MMP9).
- Piperazine (PIPZ; MMPII inhibitor; Calbiochem-EMD Chemicals Inc.) is a potent, reversible, broad range inhibitor of matrix metalloproteinases. PIPZ inhibits MMP1(IC50=24 nM), MMP3 (IC50=18.4 nM), MMP7 (IC50=30 nM), and MMP9 (IC50=2.7 nM).
- MMP3 inhibitor (MMP3i; stromelysin-1 inhibitor; Calbiochem-EMD Chemicals Inc.) inhibits MMP3 (IC50=5 nM).
- MMP9 inhibitor (MMP9i; Calbiochem-EMD Chemicals Inc.) is a cell-permeable, potent, selective, and reversible MMP9 inhibitor (IC50=5 nM). It inhibits MMP1 (IC50=1.05 μM) and
- MMP13 (IC50=113 nM) only at much higher concentrations.

In one embodiment, the inhibitor is an inhibitor of the heterotrimeric G-protein complex. In some embodiments, this inhibitor may be selected from the following list:

- Pertussis toxin (PTX), from *Bordetella pertussis*, in buffered aqueous glycerol solution, catalyzes the ADP-ribosylation of the a subunits of the heterotrimeric G proteins Gi, Go, and Gt. This prevents the G protein heterotrimers from interacting with receptors, thus blocking their coupling and activation.
- BIM-46174 is a G-protein inhibitor kindly provided by IPSEN Innovation (91940 Les Ulis, France). The imidazo-pyrazine derivative BIM-46174 acts as a selective inhibitor of heterotrimeric G-protein complex. BIM-46174 prevents the heterotrimeric G-protein signaling linked to several GPCRs mediating (a) cyclic AMP generation (Gas), (b) calcium release (Gaq), and (c) cancer cell invasion by Wnt-2 frizzled receptors and high-affinity neurotensin receptors (Gao/i and Gaq).

BIM-23127 is a specific neuromedin B receptor inhibitor from Tocris Bioscience (Tocris House, 10 Centre Moorend Farm Avenue, Bristol, BS11 0QL, United Kingdom). BIM-23127 is a D-amino-acid substituted cyclo-somatostatin octapeptide analog. The present inventors have demonstrated that the GPCR neuromedin B specific antagonist BIM-23127 dose-dependently inhibited Neu1 activity associated with HTC-IR cells and RawBlue cells. Due to the role of NMBR in inducing MMP9 elastase activity and subsequent Neu1 enzymatic activity, it was hypothesized that NMBR inhibition using BIM-23127 would suppress Neu1 sialidase activity in GPCR agonist-stimulated and insulin-stimulated HTC-IR and HTC-WT cells. BIM-23127 significantly inhibited Neu1 sialidase activity induced by insulin, bombesin, bradykinin, angiotensin I and angiotensin II in HTC-IR and HTC-WT cells. Insulin and the GPCR agonists were used at a concentration of 10 μg/mL and BIM-23127 at 50 μg/mL.

In one embodiment, the inhibitor is an inhibitor of Neu1 sialidase, suitably OP or an analogue thereof. In one embodiment, the inhibitor is OP administered intravenously or via inhalation.

In various embodiments an analogue of oseltamivir is a compound according to any one of formulas A-F:

Formula A

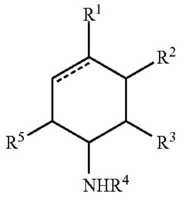

wherein, $R^1$ is halo or $COOR^6$;

$R^2$ is OH or $OR^7$;

$R^3$ is OH, $OR^8$ or $N_3$;

$R^4$ is H or $C_{1-6}$acyl;

$R^5$ is $OC_{1-6}$alkyl, $SC_{1-6}$alkyl, OH, SH, halo, $N_3$, $NH_2$, $NHC_{1-6}$alkyl or $NHPG^4$ or $R^4$ and $R^5$ are linked, together with the atoms to which they are attached, to form an oxazoline ring;

$R^6$ is $C_{1-6}$alkyl;

$R^7$ and $R^3$ are the same or different and are independently $C_{1-6}$alky, $C_{1-6}$ acyl or $PG^5$, or Rand $R^3$ are joined together with the oxygen atoms to which they are attached, to form a 5-membered cyclic ketal that is substituted on the carbon between the oxygen atoms by one or two $C_{1-6}$alkyl (preferably dimethy or diethyl ketal);

$PG^4$ and $PG^5$ are independently protecting groups.

---- represents a single or double bond and one or more hydrogens in the $C_{1-6}$alkyl and/or $C_{1-6}$acyl groups is/are optionally replaced with F;

Formula B

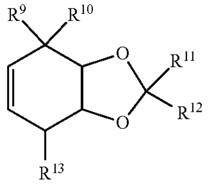

wherein $R^9$ is $COOR^{14}$ $R^{10}$ is H, OH or $OC_{1-6}$acyl;

$R^{13}$ is $NHC_{1-6}$acyl;

or the O in $R^{10}$ and the N in $R^{13}$ are joined by a covalent bond;

$R^{11}$ and $R^{12}$ are independently $C_{1-6}$alkyl;

$R^{14}$ is $C_{1-6}$alkyl, and one or more of the hydrogen atoms in the $C_{1-6}$alkyl and/or $C_{1-6}$acyl groups is/are optionally replaced with F;

Formula C

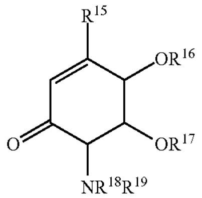

wherein, $R^{15}$ is COOEt, COOMe, COOiPr, COOnPr, $COOCH_2C≡CH$, C(O)H, C(O)OH, $C(O)O^-$, $CCl_3$, CN, C≡CH, $CH_2C≡CH$ or $CH_2OH$;

$R^{16}$ and $R^{17}$ are independently H, $C_{1-6}$alky, $C_{1-6}$acyl or a suitable protecting group, or $R^{16}$ and $R^{17}$ are joined to form a suitable protecting group such as, a cyclic ketal which may be optionally substituted on the carbon atom between the oxygen atoms by one or two $C_{1-6}$alkyl groups.

$R^{18}$ and $R^{19}$ are independently H, $C_{1-6}$alky, $C_{1-6}$acyl or a suitable protecting group or $R^{18}$ and $R^{19}$ are joined to form a suitable protecting group;

wherein one or more hydrogens in $R^{15}$, $R^{16}$, $R^{17}$ $R^{18}$ and/or $R^{19}$ is are optionally replaced with F;

Formula D

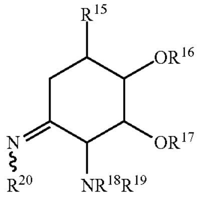

wherein, $R^{15}$ is COOEt, COOMe, COOiPr. COOnPr, $COOCH_2C≡CH$, C(O)H, C(O)OH, $C(O)O^-$, $CCl_3$, CN, C≡CH, $CH_2C≡CH$ or $CH_2OH$;

$R^{16}$ and $R^{17}$ are independently H, $C_{1-6}$alky, $C_{1-6}$acyl or a suitable protecting group, or $R^{16}$ and $R^{17}$ are joined to form a suitable protecting group such as, a cyclic ketal which may be optionally substituted on the carbon atom between the oxygen atoms by one or two $C_{1-6}$alkyl groups.

$R^{18}$ and $R^{19}$ are independently H, $C_{1-6}$alky, $C_{1-6}$acyl or a suitable protecting group or $R^{18}$ and $R^{19}$ are joined to form a suitable protecting group; and $R^{20}$ is a group that is removed under reduction or hydrogenation reaction conditions or $R^{20}$ is a suitable acid labile protecting group, for example $R^{20}$ is OH, R, O—R, O(C)—R. $Si(R)_3$, $NO_2$, $NH_2$, $N(R)_2$, $S(O)_2R$ or $S(O)_2OR$, wherein each R is independently alkyl, aryl or heteroaryl and various substituted derivatives thereof.

wherein one or more hydrogens in $R^{15}$, $R^{16}$, $R^{17}$ $R^{18}$, $R^{19}$ and/or $R^{20}$ is/are optionally replaced with F;

Formula E

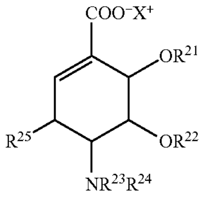

wherein,

X+ is a cation;

$R^{21}$ and $R^{22}$ are independently H, $C_{1-6}$alkyl or $C_{1-6}$acyl, or $R^{21}$ and $R^{22}$ are joined together with the atoms to which they are attached, to form a 5-10-membered ring that is unsubstituted or substituted with one or more halo or $C_{1-6}$alkyl;

$R^{23}$ and $R^{24}$ are independently H, $C_{1-6}$alkyl and $C_{1-6}$acyl;

$R^{25}$ is $OR^{26}$, $NR^{27}R^{28}$, =O or $=NR^{29}$;

$R^{26}$ is H, $C_{1-6}$alkyl or $C_{1-6}$acyl;

$R^{27}$ and $R^{28}$ are independently H, $C_{1-6}$alkyl or $C_{1-6}$acyl;

$R^{29}$ is H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}$acyl or $NHC_{1-6}$acyl, or $R^{29}$ and one of $R^{23}$ and $R^{24}$ form a linker group "-A-C(O)—" to provide a compound of the formula:

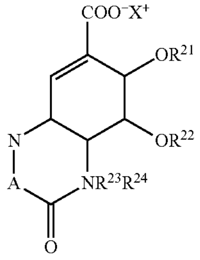

wherein A is O or NH; and one or more available hydrogens in $R^{21}$, $R^{22}$, $R^{23}$, $R^{24}$, $R^{25}$, $R^{26}$, $R^{27}$, $R^{28}$ and/or $R^{29}$ is/are optionally replaced with F;

or

Formula F

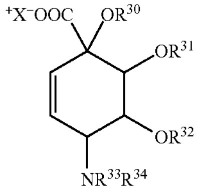

wherein,

X+ is a cation $R^{30}$ is H, $C_{1-6}$alkyl or $C_{1-6}$acyl;

$R^{31}$ and $R^{32}$ are independently F, $C_{1-6}$alkyl or $C_{1-6}$acyl or $R^{31}$ and $R^{32}$ are joined together, with the atoms to which they are attached, to form a 5-10-membered ring that is unsubstituted or substituted with one or more of halo or $C_{1-4}$alkyl;

$R^{33}$ and $R^{34}$ are independently H, $C_{1-6}$alkyl or $C_{1-6}$acyl; and one or more available hydrogen atoms in $R^{30}$, $R^{31}$, $R^{32}$, $R^{33}$ and/or $R^{34}$ is/are optionally replaced with F or salts, solvates, prodrugs, stereoisomers or isotope-labelled forms thereof or mixtures thereof.

In a further embodiment the compound is a compound of formula E and R25 is $=NR^{29}$.

In a further aspect of the invention the analogue is:

A1

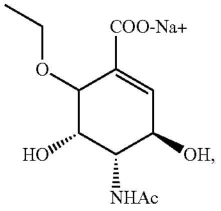

A2

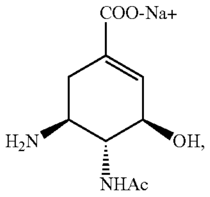

A3

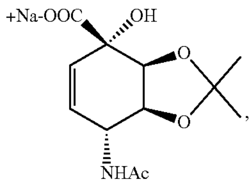

A4

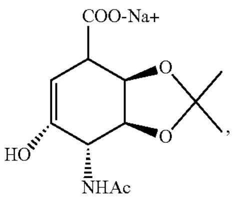

-continued

A5

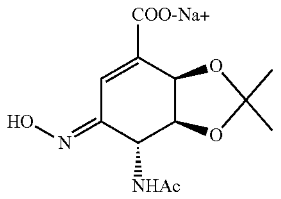

or

A6

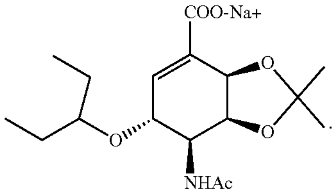

.

In still a further aspect the corresponding chemical names for the above structure are:

Sodium; 4-acetylamino-6-ethoxy-3,5-dihydroxy-cyclohex-1-enecarboxylate (A1);

Sodium; 4-acetylamino-5-amino-3-hydroxy-cyclohex-1-enecarboxylate (A2);

Sodium; 7-acetylamino-4-hydroxy-2,2-dimethyl-3a,4,7,7a-tetrahydro-benzo[1,3]dioxole-4-carboxylate (A3);

Sodium; 7-acetylamino-6-hydroxy-2,2-dimethyl-3a,4,7,7a-tetrahydro-benzo[1,3]dioxole-4-carboxylate (A4);

Sodium; 7-acetylamino-6-hydroxyimino-2,2-dimethyl-3a,6,7,7a-tetrahydro-benzo[1,3]dioxole-4-carboxylate (A5) and Sodium; 7-acetylamino-6-(1-ethyl-propoxy)-2,2-dimethyl-3a,6,7,7a-tetrahydro-benzo[1,3]dioxole-4-carboxylate (A6).

While the analogues described above are shown in the sodium salt form it will be understood by a person of skill in the art that other salt forms are possible and are included in the scope of the invention. Additionally, caboxylate ester of lower alkyl (C1-6 alkyl) forms are also included in the scope of the invention "Alkyl" as used herein, whether it is used alone or as part of another group means straight or branched chain saturated alkyl groups. "$C_{1-6}$alkyl" refers to an alkyl groups having 1, 2, 3, 4, 5 or 6 carbon atoms.

"Acyl" as used herein, whether it is used alone or as part of another group means straight or branched chain saturated acyl groups. "$C_{1-6}$acyl" refers to an acyl group having 1, 2, 3, 4, 5, or 6 carbon atoms.

"Halo" as used herein refers to a halogen atom and includes F, Cl, Br and I.

A wavy bond, such as, "~~~" indicates that the stereochemistry of the bond is variable. For example when attached to a double bond, this symbol indicates that the group bonded to the double bond is in either the cis or trans configuration or the compound comprises a mixture of the two configurations.

"Optionally substituted" as used herein means that the referenced group is unsubstituted or substituted with one or more groups, for example optional substituents may include $C_{1-6}$alkoxy, nitro, cyano, hydroxyl and amino, and protected forms thereof.

The term "pharmaceutically acceptable salt" means an acid addition salt or basic addition salt of a neutral compound, which is suitable for, or compatible with, the treatment of a subject.

The term "pharmaceutically acceptable acid addition salt" as used herein means any non-toxic organic or inorganic salt of any base compound of the invention, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the formula I, for laboratory use, or for subsequent conversion to a pharmaceutically acceptable acid addition salt. In embodiments of the invention, the pharmaceutically acceptable acid addition salt is the hydrochloride salt.

The term "pharmaceutically acceptable basic addition salt" as used herein means any non-toxic organic or inorganic salt of any acid compound or any of its intermediates. If a compound comprises an acidic group, for example a carboxylic acid, a basic addition salt is formed by adding a suitable base. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. Such salts may exist in either hydrated solvated or substantially anhydrous form. The selection of the appropriate salt will be known to one skilled in the art. In an embodiment of the invention the pharmaceutically acceptable basic addition salt is an alkali metal salt such as a sodium salt.

The formation of a desired compound salt is achieved using standard techniques. For example, the neutral compound is treated with an acid or base in a suitable solvent and the formed salt is isolated by filtration, extraction or any other suitable method.

The analogues of the invention may further be formulated as solvates. The term "solvate" refers to incorporation of molecules of a suitable solvent in the crystal lattice of a compound. A suitable solvent is physiologically tolerable at the dosage administered. Examples of suitable solvents are ethanol, water and the like. When water is the solvent, the molecule is referred to as a "hydrate". The formation of solvates of the analogues of the invention will vary depending on the compound and the solvate. In general, solvates are formed by dissolving the compound in the appropriate solvent and isolating the solvate by cooling or using an antisolvent. The solvate is typically dried or azeotroped under ambient conditions.

Analogues of oseltamivir as described above may further include prodrug forms. In general, such prodrugs will be functional derivatives of a compound of the formula I which are readily convertible in vivo into the compound from which it is notionally derived. Prodrugs of the analogues may be conventional esters formed with available hydroxy, or amino group. For example, an available OH or nitrogen in a compound may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the analogues are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The term "isotopic label" refers to an isotopic form of an atom that is other than the most abundant form of that atom in nature. For example $^{2}H$, $^{3}H$, $^{13}C$ $^{14}C$ or a radioactive halogen such as $^{125}I$. A labelled compound of the invention may be prepared using standard methods known in the art. For example, tritium may be incorporated into a compound using standard techniques, for example by hydrogenation of a suitable precursor to a compound of the invention using tritium gas and a catalyst. Alternatively, a compound containing a radioactive iodo may be prepared from the corresponding trialkyltin (suitably trimethyltin) derivative using standard iodination conditions, such as [$^{125}I$] sodium iodide in the presence of chloramine-T in a suitable solvent, such as dimethylformamide. The trialkyltin compound may be prepared from the corresponding non-radioactive halo, suitable iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

Analogues of the invention may include protecting groups on various chemical moieties, substitution of the protecting group and/or deprotection of those chemical moieties would be known to a person of skill in the art and analogues containing such modifications would also be included in the scope of the invention.

The terms "protecting groups" or "protective groups" or "PG" or the like, refer to a chemical moiety which protects or masks a reactive portion of a molecule generally for the purpose of preventing side reactions in those reactive portions of the molecule while manipulating or reacting different portions of the molecule. After the manipulation or reaction is complete, the protecting group may be removed under conditions that do not degrade or decompose the remaining portions of the molecule. The selection of suitable protecting groups can be made by a person of skill in the art. Many conventional protecting groups are known in the art, for example as described in "Protective Groups in Organic Chemistry" McOmie, J. F. W. Ed. Plenum Press, 1973, In Greene, T. W. and Wuts, P. G. M., "Protective Groups in Organic Synthesis" John Wiley & Sons, 3rd Edition, 1999 and in Kocienski, P. "Proteciting Groups", 3rd Edition, 2003, Georg Thieme Verlag (The Americas).

Analogues of the invention may include asymmetric centres. Where the analogues of the invention poses more than one asymmetric centre, they may exist as diastereomers. It is to be understood that all such isomers and mixtures thereof in any proportion are encompassed within the scope of the present invention. It is to be understood that while the stereochemistry of the compounds of the invention may be as provided for in any given compound listed herein, such compounds of the invention may also contain certain amounts (e.g. less than 20%, preferably less than 10%, more preferably less than 5%) of compounds of the invention having alternate stereochemistry.

In other embodiments, the Neu 1 sialidase inhibitor is 2-deoxy-2,3-dehydro-N-acetylneuraminic acid (DANA) or an analogue of DANA.

In an embodiment of the invention the analogues of DANA are of the Formula G

G

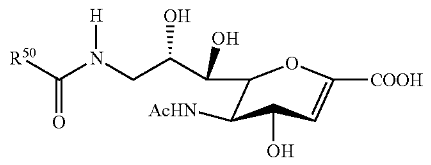

Wherein $R^{50}$ is $C_{1-6}$alkyl wherein the alkyl may be straight or branched aliphatic or the alkyl group may be a cyclic alkyl group.

In particular, $R^{50}$ is methyl, propyl butyl, cyclopropyl, cyclopentyl, cyclohexyl, 2 butyl, i-butyl, t-butyl, 3-pentyl, i-propyl.

In a particular aspect of the invention R is methyl, propyl, butyl, 2-butyl, cylopentyl, cyclohexyl.

In an embodiment of the invention the DANA analogue is:

B1

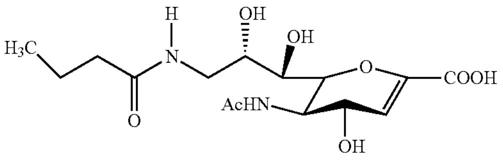

B2

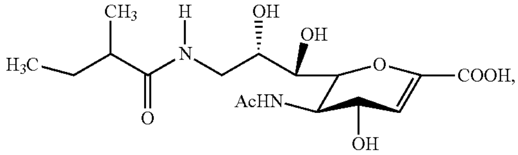

,

B3

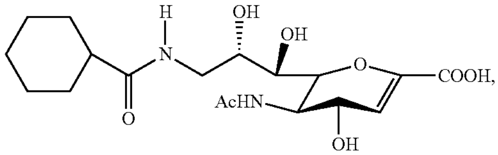

,

B4

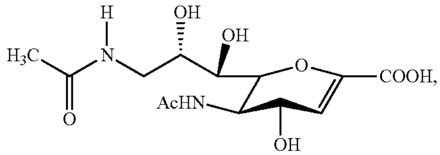

,

B5

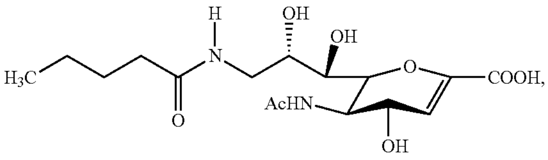

,

-continued

B6

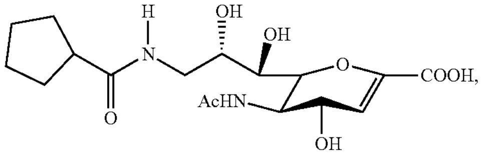

B7

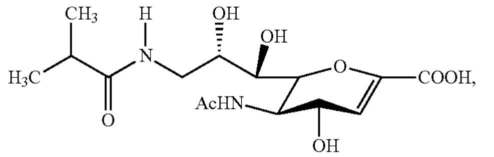

B8

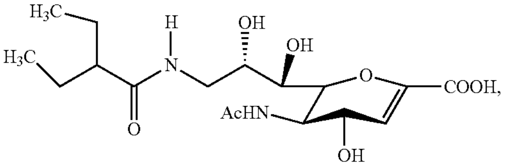

B9

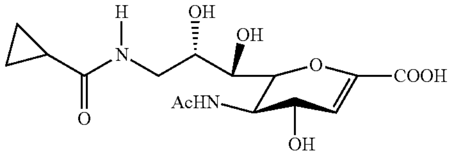

or

B10

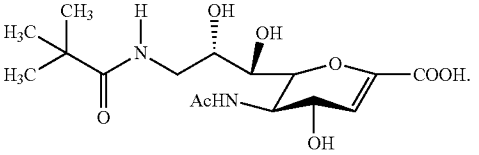

Coronavirus Activated Pro-Inflammatory Cytokine and Bradykinin Storms

Many patients infected with COVID-19 develop ARDS. COVID-19 infected lung cells cause injury that triggers alveolar macrophages. ARDS is a type of respiratory failure characterized by rapid onset of widespread inflammation in the lungs. Symptoms include shortness of breath, rapid breathing, and bluish skin coloration. Among those who survive, a decreased quality of life is relatively common. ARDS is a form of fluid accumulation in the lungs not explained by heart failure (noncardiogenic pulmonary edema). It is typically provoked by an acute injury to the lungs that results in flooding of the lungs' microscopic air sacs responsible for the exchange of gases such as oxygen and carbon dioxide with capillaries in the lungs. Additional common findings in ARDS include partial collapse of the lungs (atelectasis) and low levels of oxygen in the blood (hypoxemia). The clinical syndrome is associated with pathological findings including pneumonia, eosinophilic pneumonia, cryptogenic organizing pneumonia, acute fibrinous organizing pneumonia, and diffuse alveolar damage (DAD). Of these, the pathology most commonly associated with ARDS is DAD, which is characterized by a diffuse inflammation of lung tissue. The triggering insult to the tissue usually results in an initial release of chemical signals and other inflammatory mediators secreted by local epithelial and endothelial cells. Neutrophils and some T-lymphocytes quickly migrate into the inflamed lung tissue and contribute in the amplification of the phenomenon. Typical histological presentation involves diffuse alveolar damage and hyaline membrane formation in alveolar walls.

A mechanism for pathogen molecule-induced TOLL-like receptor (TLR) activation and cell function, which is critically dependent on Neu1 sialidase activity associated with TLR ligand treated live primary macrophage cells and macrophage and dendritic cell lines (Amith, Jayanth et al. (2009) Glycoconj J 26 p 1197-1212) has been reported. A membrane controlling mechanism that is initiated by ligand binding to TLR-2, -3 and -4 to induce Neu1 sialidase activity within minutes was shown in live primary bone marrow (BM) macrophage cells and macrophage and dendritic cell lines.

Central to this process is that Neu1 and not Neu2,-3 and -4 forms a complex with TLR-2,-3 and -4 on the cell surface of naïve macrophage cells. Neuraminidase inhibitors BCX1827, 2-deoxy-2,3-dehydro-N-acetylneuraminic acid (DANA), zanamivir and oseltamivir carboxylate have a limited significant inhibition of the LPS-induced sialidase activity in live BMC-2 macrophage cells, but Tamiflu (OP) completely blocks this activity. OP inhibits LPS-induced sialidase activity in live BMC-2 cells with an IC50 of 1.2 μM compared to an IC50 of 1015 μM for its hydrolytic metabolite oseltamivir carboxylate. OP blockage of LPS-induced Neu1 sialidase activity is not affected in BMC-2 cells pretreated with anti-carboxylesterase agent clopidogrel. Endotoxin LPS binding to TLR4 induces Neu1 with subsequent activation of NFκB and the production of nitric oxide and proinflammatory IL-6 and TNFα cytokines in primary and macrophage cell lines. Hypomorphic cathepsin A mice with a secondary Neu1 deficiency respond poorly to LPS induced pro-inflammatory cytokines compared to the wild-type or hypomorphic cathepsin A with normal Neu1 mice lines (Amith, Jayanth et al. (2009) Glycoconj J 26 p 1197-1212)

GPCR agonists bombesin, bradykinin, lysophosphatidic acid (LPA), cholesterol, angiotensin-1 and -2, but not thrombin induce Neu1 activity in live macrophage cell lines and primary bone marrow macrophage cells from wild-type (WT) mice but not from Neu1-deficient mice (Abdulkhalek, Guo et al. Cellular Signalling 24 (2012) 2035-2042). GPCRs exhibit key regulatory functions in innate and acquired immunity. There is evidence for a crosstalk between GPCR and TOLL-like receptor (TLR) signaling pathways. Under, this signaling paradigm, ligand binding to the receptor on the cell surface induces a conformational change of the receptor to initiate GPCR-signaling via GPCR Gα subunit proteins and MMP-9 activation to induce Neu1. Activated Neu1, tethered to TLR on the cell surface, targets and hydrolyzes sialyl α-2-3-linked β-galactosyl residues at the ectodomain of TLR receptors. Taken together, these findings predict a prerequisite desialyation of TLR receptors caused by activated Neu1 enabling the removal of a steric hindrance to receptor association with subsequent activation of TLR receptors and cellular signaling. This molecular organizational GPCR signaling platform is posited to be an initial processing stage for GPCR agonist-induced transactivation of TLRs and subsequent downstream NFκB signaling.

Thus, there is evidence that the activation of Neu1 sialidase in complex with TLR-2,-3 and -4 receptors on the cell surface of macrophages is inhibited by the neuraminidase inhibitor OP. Also, OP significantly inhibited endotoxin LPS induced NFκB activation and the production of nitric oxide and pro-inflammatory IL-6 and TNFα cytokines in primary or macrophage cell lines. On the basis that Mas GPCR potentiates receptor biased-induced TLR transactivation via NMBR-Neu1-MMP9 crosstalk on the cell surface alveolar macrophages, then OP will inhibit the pro-inflammatory responses in the lungs and reduce the inflammatory process.

In addition, inhibition of the desialylation of the RBD-ACE2-B0AT1 complex for COVID-19 binding would inhibit the viral infectivity of the lung cells.

The Examples evidence that the inflammatory mechanism outlined above is initiated by the COVID S protein and variants thereof.

For patients already infected by the corona virus and exhibiting signs and symptoms of impending respiratory failure, by interfering with a number of conserved GPCR and toll-like receptor signaling cascades that have been implicated in the pathophysiology of ARDS, intravenous OP in combination with aspirin can ameliorate the cytokine storm that has been implicated in causing alveolar damage and ultimately respiratory failure and death from ARDS.

Without limiting the generality of the foregoing, a cytokine profile associated with COVID-19 disease severity is characterised by increased interleukin (IL)-2, IL-7, granulocyte-colony stimulating factor (G-CSF), interferon-γ inducible protein-10 (IP-10, or CXCL10), monocyte chemoattractant protein 1 (MCP-1/CCL2), macrophage inflammatory protein 1-α (MIP-1a), and tumour necrosis factor-α (TNF-α) and, in various embodiments, administering treatments as described herein may results in an observable decrease in levels of one or more of these cytokines in patient serum/plasma. Predictors of fatality from a recent retrospective, multicentre study of 150 confirmed COVID-19 cases in Wuhan, China, included elevated ferritin (p<0-001; measures how much iron is in the body) and IL-6 (p<0-0001), In some embodiments, treatment as described herein and, in particular, treatment with OP results in an observable decrease in levels of IL-6, TNFα, and/or G-CSF in patient serum/plasma.

Inflammatory Immune Response, Sepsis and ARDS

Sepsis is an inflammatory immune response triggered by an infection, which may be bacteria, fungal, viral or protozoan in origin. Sepsis is an inflammatory immune response associated with various symptoms including fever, low body temperature and blood pressure, rapid breathing and confusion. Severe sepsis is associated with multiple organ dysfunction syndrome, including ARDS in the lungs. Thus in one embodiment, the present invention provides for treating, preferably at an early stage, a sepsis patient with an inhibitor of NEU-1 to prevent respiratory failure and developing ARDS.

Use of OP Administered so as to Avoid Conversion to Oseltamivir Carboxylate, Optionally in Combination with Aspirin, as Treatment for COVID-19 Infection Oseltamivir phosphate, (3R,4R,5S)-4-acetylamino-5-amino-3-(1-ethylpropoxy)1-cyclohexene-1-carboxylic acid, ethyl ester, phosphate (1:1), is a non-hygroscopic pro-drug of an active metabolite for the treatment of viral influenzae, oseltamivir carboxylate. Oseltamivir Phosphate (OP) is soluble in water. OP is converted to oseltamivir carboxylate via first pass hepatic esterases when taken orally. Oseltamivir carboxylate is the active moiety useful in the treatment of viral influenza and targets viral neuraminidase. OP is sold by Hoffman la Roche under the trade name Tamiflu.

OP is not currently used therapeutically for any approved indications. Rather, it is used only as a prodrug that is converted to the active metabolite oseltamivir carboxylate when taken orally. The present inventors have identified that the prodrug, OP, is active against mammalian neuraminidase 1, making it relevant as an anti-viral agent in its own right and, in particular, in preventing ARDS in patients that are infected with the COVID-19 virus and are exhibiting signs and symptoms of impending respiratory failure.

Based on the highly conserved role of mammalian neuraminidase 1 in regulating the dimerization of a number of cell surface receptors, including GPCRS, and their implicated role in fostering dimerization of the ACE-2 cell surface receptor critical to viral cellular entry, intravenous OP can block the dimerization process and interfere with viral cellular entry.

The OP is administered so as to inhibit or avoid conversion to oseltamivir carboxylate. In this context, "inhibit" conversion may mean that >10%, >25%, >50%, preferably >75% and more preferably >90% of OP is converted to oseltamivir carboxylate in vivo prior to cellular uptake. OP may be administered intravenously or via aerosol inhalation directly into the lungs in order to inhibit or avoid conversion to oseltamivir carboxylate.

TOLL-like receptor (TLR) activation is controlled by Neu1 sialidase activation. Studies have shown that Neu1 is already in complex with the TOLL-like receptors, and activation is induced upon ligand binding of the natural ligands to their respective receptors. In addition, activated Neu1 specifically hydrolyzes (α-2,3-sialyl residues linked to β-3-galactoside, which are distant from the ligand binding site. This removes steric hindrance to receptor dimerization, and leads to subsequent signalling pathways.

It has been found that the neuraminidase inhibitor, oseltamivir phosphate, specifically inhibits TLR ligand-induced Neu1 activity on the cell surface of macrophage and dendritic cells, and subsequently blocks TLR ligand induced NFkB activation, nitric oxide (NO) production and pro-inflammatory cytokines. In addition, other purified neuraminidase inhibitors such as BCX-1827, DANA (2-deoxy-2,3-dehydro-N-acetylneuraminic acid}, zanamivir (4-guanidino-Neu5Ac2en}, and oseltamivir carboxylate had a limited effect on inhibition of lypopolysaccharide (LPS) induced sialidase activity in live BMC-2 macrophage cells at 1-2 mM compared to the LPS positive control.

Other studies using recombinant soluble human sialidases have shown that oseltamivir carboxylate scarcely inhibited the activities of the four human sialidases even at 1 mM, while zanamivir significantly inhibited the human Neu2 and Neu3 sialidases in the micromolar range. Furthermore, using lysates from mature dendritic cells, others have found that zanamivir completely inhibited Neu1 and Neu3 sialidase activity at 2 mM.

Interestingly it has been found that OP was the most potent compared to the other neuraminidase inhibitors in inhibiting the sialidase activity associated with TLR ligand treated live macrophage cells whereas this compound is known to be ineffective as an antiviral in vitro because its antiviral activity is achieved by its hydrolytic metabolite oseltamivir carboxylate.

To further elucidate the inhibitory capacity of OP and its hydrolytic metabolite oseltamivir carboxylate, the 50% inhibitory concentration (IC50) of each compound was determined by plotting the decrease in sialidase activity against the log of the agent concentration. It was shown that oseltamivir phosphate had an IC50 of 1.175 μM compared to an IC50 of 1015 μM for oseltamivir carboxylate. These data clearly illustrate that oseltamivir phosphate is 1000-fold more potent than its hydrolytic metabolite in inhibiting the sialidase activity associated with TLR ligand treated live BMC-2 macrophage cells.

It is possible that OP could be transported through the cell membrane by a P-glycoprotein, where the hydrolytic activation could be catalyzed by carboxylesterase. The anti-platelet agent clopidogrel has been previously determined to inhibit the hydrolysis of OP by carboxylesterase as much as 90%. To determine whether the OP is hydrolysed in the cell in this live cell assay system, live BMA macrophage cells were pre-treated with clopidogrel bisulfate at 280 μM and 500 μM for 2 min followed with 5 μg/ml of endotoxin lipopolysaccharide (LPS) in the presence or absence of 400 μM pure OP. The results indicated that the anti-carboxylesterase agent clopidogrel had no effect on OP's capacity to inhibit LPS induced sialidase activity.

Together, these results suggest that OP is a potent inhibitor of the sialidase associated with TLR ligand treated live macrophage cells.

In some embodiments, analogues of OP that act as Neu1 sialidase inhibitors may be used in the composition and methods of the present invention.

Methods of preparing oseltamivir and derivatives or analogues thereof, have been described in the patent literature, for example, in PCT publications WO 2009/137916 and WO 2011/047466, incorporated herein by reference. WO 2009/137916 and WO 2011/047466 further describe intermediates useful for the process for preparing oseltamivir and derivatives thereof. Methods of preparing oseltamivir and derivatives or analogues thereof can also be found in PCT publication WO2013/063679, U.S. Pat. No. 10,350,188 B2; and European Patent No. 2773340 B. In various embodiments, the analogue may be selected from those identified above.

Analogues of oseltamivir and DANA may be preferred based on higher potency than OP and DANA. Without limiting the generality of the foregoing, in preferred embodiments, an analogue of oseltamivir may be selected from analogs A2 and A5 identified above, again without limiting the generality of the foregoing, in preferred embodiments, an analogue of DANA may be selected from B1 and B3.

In one embodiment, early blocking of signaling cascades predicted to be upregulated after COVID-19 viral infection using an infusion regimen of OP, preferably in combination with aspirin, is used to prevent the development of ARDS in patients exhibiting early signs of acute respiratory failure from infection with COVID-19.

It has been found that OP in combination with aspirin can improve the efficacy of the agents and can improve anti-inflammatory activity in cells that are stimulated by COVID-19 S protein and COVID-19 variant S-protein treatments.

It has further been found that OP in combination with aspirin can improve the efficacy of the agents and can improve anti-COVID-19 and its variants infectivity in cells that are bound to ACE-2 receptors.

The present inventors have demonstrated that aspirin can inhibit Neu-1 sialidase and potentiates the ability of OP to inhibit mammalian neuraminidase 1. Thus, aspirin in combination with OP can inhibit mammalian neuraminidase 1 in a synergistic manner. In one embodiment, aspirin, preferably administered orally, is added to an intravenous or inhalation regimen of OP.

Carriers suitable for the preparation of intravenous formulations will be known to those of skill in the art. For example, pharmaceutical carriers suitable for injection can include but are not limited to sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Suitable methods for preparing formulations for inhalation will also be known to those of skill in the art, who will be familiar with inhalation systems for the aerosolization of drugs, including nebulizers, pressurized metered-dose inhalers and dry powder inhalers, and carrier systems, including polymeric particulate and lipid based carriers.

Suitably, OP is formulated in a sterile normal saline. OP may be formulated as a lyophilized powder for storage and shipment. The lyophilized OP can then be reconstituted with sterile normal saline for immediate use as a sterile intravenous injection. Lyophilized powder can also be formulated for inhalation via methods known in the art.

Treatment Protocol

Patients with confirmed infection with COVID-19 and its variant viruses or patients with suspected infections exhibiting signs of respiratory distress would be eligible for the treatment. Ideally, treatment should begin as soon as possible once diagnosis is confirmed and prior to the development of frank respiratory failure. Ideally, because the development of frank respiratory failure and ARDS can occur rapidly with COVID-19 and its variant infections, treatment should begin immediately with the first signs of respiratory compromise.

OP can suitably be administered in daily doses of between 100 mg and 1000 mg, preferably between 300 mg and 500 mg.

In one embodiment, in addition to treatment with intravenous OP, patients are administered aspirin, suitably via oral administration. Aspirin can suitably be administered at a dose of between 100 mg and 1000 mg per day, preferably between 400 mg and 600 mg per day.

In an exemplary protocol, treatment comprises administration of OP at a dose of about 200 mg given by IV infusion over four hours followed immediately by an additional 200 mg dose of OP given over 24 hours by continuous infusion. If there are signs of clinical improvement and/or no clinical deterioration, an additional dose of intravenous OP at a dose of 200 mg given over 24 hours could also be administered by treating clinician. In one exemplary protocol, the patient is further administered aspirin at a dose of 500 mg po daily.

In a preferred embodiment, an initial bolus is provided followed by continuous infusion to keep the suppression of NEU-1 as constant as possible during the critical period of predicted inflammatory storm from initial infection when the risk for development of ARDS is substantial.

The lyophilized OP can suitably be provided in dosages of 200 mg to be readily reconstituted e.g. in sterile glass vials.

In other embodiments, the OP may be provided in preloaded syringes. The OP may also be provided in preloaded inhalers.

In one embodiment, the OP is administered regularly, suitably daily, until the patient tests negative for the coronavirus. In one embodiment, the OP is administered daily for between 1 and 14 days, in one embodiment, between 1 and 7 days in one embodiment between 1 and 3 days.

In one embodiment, there is provided a novel therapeutic strategy employing the combination of intravenous OP, optionally in combination with aspirin, in patients with COVID-19 and its variants virus infection who are exhibiting clinical signs suggestive of respiratory compromise.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

Section headings used herein are for organizational purposes only and are not to be construed as limiting the subject matter. The embodiments described above and illustrative and are intended to be exemplary only. The scope is indicated by the appended claims.

EXAMPLES

Example 1

RAW-Blue™ cells (mouse macrophage reporter cell line, Invivogen, San Diego CA) derived from RAW 264.7 macrophages were grown in a culture medium under the selection of Zeocin™. The cells stably express a secreted embryonic alkaline phosphatase (SEAP) gene inducible by NF-kB and AP-1 transcription factors. Upon stimulation, RAW-Blue™ cells activate NF-kB and AP-1 leading to the secretion of SEAP, which is detectable and measurable using QUANTI-Blue™, a SEAP detection medium (Invivogen). Supernatants (20 uL) after 24 hr reaction from treated RawBlue cells is added to QuantiBlue reagent (180 uL), and the readout of color reaction was done after 6 hrs. QUANTI-Blue™ is a colorimetric enzyme assay developed to determine the activity of any alkaline phosphatase present in a biological sample (supernatants) and was prepared according to manufacturer's instructions. RAW-Blue™ cells are resistant to Zeocin™ and G418.

Figure 2A:
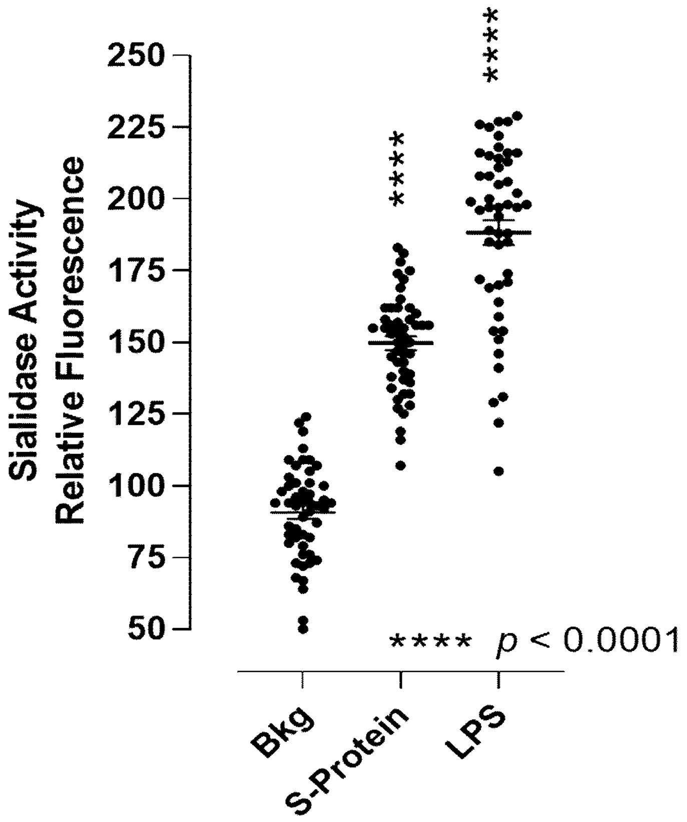
FIG. 2A shows the results of a Secreted Embryonic Alkaline Phosphatase (SEAP) reporter assay per Example 1. Sialidase activity is associated with GPCR agonist treatments of live RAW-blue macrophage cells. Cells were allowed to adhere on 12 mm circular glass slides for 24 h at 37° C. in a humidified incubator. After removing the media, 0.318 mM of 2'-(4-methylumbbelliferyl) α-d-N-acetyl-neuraminic acid (4-MUNANA) substrate in Tris buffered saline pH 7.4 was added to cells alone (background, Bkg)) or with either S-protein 20 μg/mL, 20 μg/mL endotoxin LPS.
Figure 2B:
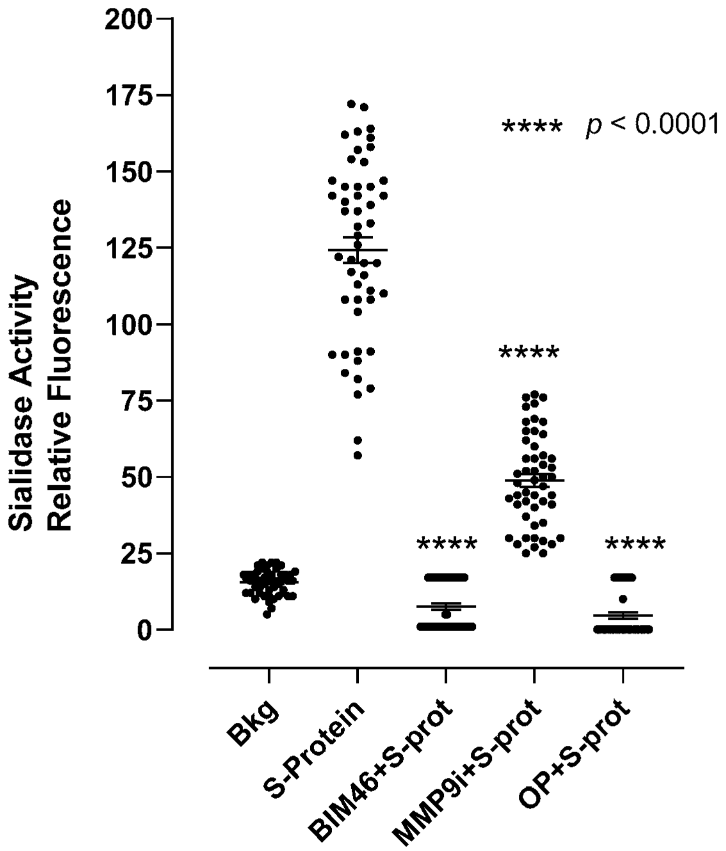
FIG. 2B shows the results of a SEAP reporter assay per Example 1. Sialidase activity in live RAW-blue macrophage cells associated with S-protein was inhibited by OP, BIM-46174 (BIM46, selective inhibitor of heterotrimeric G-protein complex) and MMP9 specific inhibitor (MMP9i). Cells were allowed to adhere on 12 mm circular glass slides for 24 h at 37° C. in a humidified incubator. After removing the media, 0.318 mM 4-MUNANA substrate in Tris buffered saline pH 7.4 was added to cells alone (background, Bkg)) or with S-protein and 200 μg/mL oseltamivir phosphate (OP), 200 μg/mL BIM-46174 (BIM46, selective inhibitor of heterotrimeric G-protein complex) or 200 μg/mL MMP9 specific inhibitor (MMP9i).
Figure 2C:
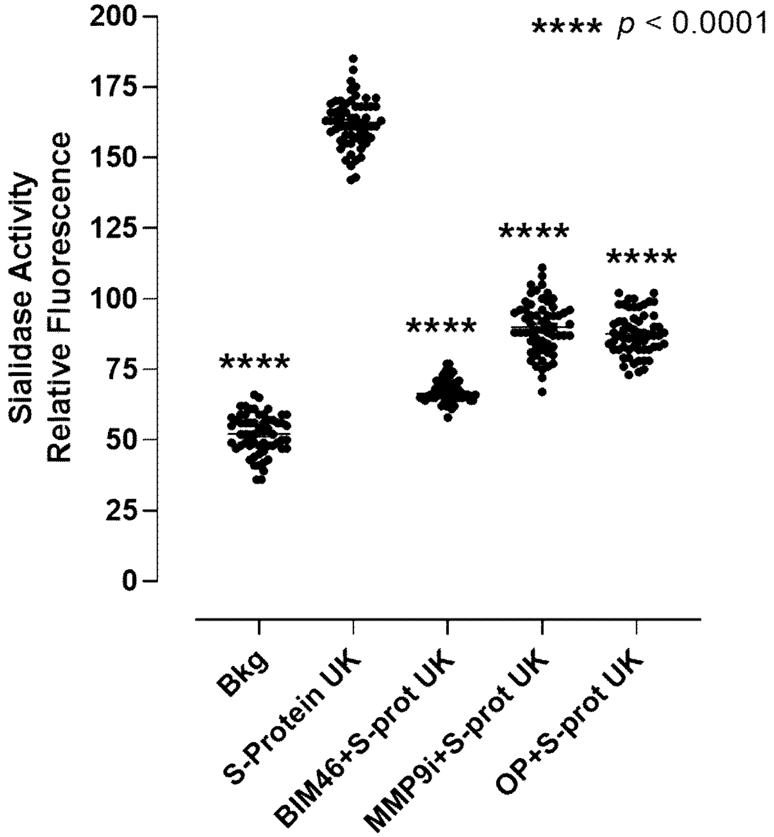
FIG. 2C shows the results of a SEAP reporter assay per Example 1. Sialidase activity in live RAW-blue macrophage cells associated with S-protein (UK variant) was inhibited by OP, BIM-46174 and MMP9i. Cells were allowed to adhere on 12 mm circular glass slides for 24 h at 37° C. in a humidified incubator. After removing the media, 0.318 mM 4-MUNANA substrate in Tris buffered saline pH 7.4 was added to cells alone (background, Bkg)) or with S-protein and 200 μg/mL OP, 200 μg/mL BIM-46174 or 200 μg/mL MMP9i.

Cells were allowed to adhere on 12 mm circular glass slides for 24 h at 37° C. in a humidified incubator. After removing the media, 0.318 mM 4-MUNANA substrate in Tris buffered saline pH 7.4 was added to cells alone (background, Bkg)) or with either S-protein 20 μg/mL, 20 μg/mL endotoxin LPS, angiotensin 1-7 (20 ug/mL) or in combination with the indicated S-protein and 200 μg/mL oseltamivir phosphate (OP), 200 μg/mL BIM-46174 (BIM46, selective inhibitor of heterotrimeric G-protein complex) or 200 μg/mL MMP9 specific inhibitor (MMP9i). Fluorescent images were taken at 2 min after adding substrate using epi-fluorescent microscopy (40× objective). The mean fluorescence surrounding the cells for each of the images was measured using Image J Software. With reference to FIGS. 2A-2C, the results are depicted as a scatter plot of data point visualization using dots to represent the fluorescence values n=50) obtained from one representative experiment of 2 separate experiments with similar results. The relative fluorescence values of each group were compared to the untreated Bkg control by ANOVA using the uncorrected Fisher's LSD multiple comparisons test with 95% confidence with indicated asterisks for statistical significance.

With reference to FIG. 2A, sialidase activity is associated with GPCR agonist treatments of live RAW-blue macrophage cells. With reference to FIGS. 2B and 2C, sialidase activity is associated with the COVID-19 S-Protein and the UK variant S-Protein, which activity is inhibited by OP, BIM-46174 and MMP9i.

Example 2

A cell suspension of 550,000 RAW-blue cells/mL in fresh growth medium was prepared, and 180 μL of cell suspension (~100,000 cells) was added to each well of a Falcon flat-bottom 96-well plate (Becton Dickinson). After different incubation times, indicated dosages of LPS, bradykinin, angiotensin 1-7, neuropeptide FF, and S-protein alone or together with indicated dose-dependent OP were added to each well. The plates were incubated at 37° C. in a 5% CO2 incubator for 18-24 h. 180 μL of QUANTI-Blue™ solution was added to each well of a flat-bottom 96-well plate, followed by 20 μL of supernatant from stimulated RAW-blue cells. The plate was incubated for 30 min to 3 h at 37° C. and the SEAP levels were determined using a spectrophotometer at 620-655 nm. Each experiment was performed in triplicate. Results are shown in FIG. 3.

Recombinant S protein and LPS triggered Sialidase activity. This activity was blocked by OP, providing evidence that the sialidase activity comes from NEU-1 as OP is a specific inhibitor of Neu-1. This activity is also inhibited by BIM-46714, an inhibitor of the heterotrimeric G protein receptor complex. These G protein-coupled receptors are found in association with ACE-2 and are likely facilitating ACE-2 receptor dimerization as well through the activation of NEU-1 in an analogous process already discovered for the Toll-like receptors.

The endotoxin LPS, Bradykinin, and Ang 1-7 all triggered increased expression of SEAP, this reporter assay being reflective of NF-kB expression and downstream induction of inflammatory molecules such as IL-6. Bradykinin is a G protein receptor agonist implicated in the cytokine storm of COVID infection. Ang 1-7 is produced by activated ACE2, which, once activated, catalyzes angiotensin II's conversion to angiotensin-(1-7). Ang 1-7 induces Sialidase activity.

OP significantly decreased the expression of SEAP activity triggered by the S protein, evidencing that NEU-1 plays a critical role in the cytokine storm induced by COVID-19 and its variants.

The present Examples provide evidence that COVID and its variants S proteins trigger Neu-1 sialidase activity and that this activity can be blocked by using a specific inhibitor of NEU-1, OP, and blocking the G protein-coupled receptors' activity complexed to the ACE-2 receptor. These receptors can also activate NEU-1, thereby facilitating ACE-2 receptor dimerization and a permissive state for viral entry into the cell.

In addition to the role played by NEU-1 in facilitating ACE-2 receptor dimerization and subsequent viral entry into the cell, NEU-1 plays a critical role in the induction of the cytokine storm implicated in COVID-19 pathogenesis and ARDS through its critical role in the activation of Toll-like receptors.

The data presented in FIGS. 3A-D support a novel organizational GPCR signaling platform tethered to TLR receptors as the initial processing stage for GPCR agonist-induced transactivation of these receptors and subsequent downstream cellular signaling. Specifically, that GPCR receptors form a complex with glycosylated TLR receptors at the ectodomain. Secondly, Neu1 may be a requisite intermediate in regulating TLR activation following ligand binding to the receptor. Thirdly, activated Neu1 by ligand binding to the receptor predicts a rapid removal of α-2,3-sialyl residues linked to β-galactosides on TLR ectodomain to generate a functional receptor. The sialidases classified as cytosolic (Neu2), plasma membrane bound Neu3 and Neu4 are not involved in the sialidase activity associated with ligand-treated live TLR-expressing cells and primary bone marrow macrophages. Fourthly, the potentiation of GPCR-signaling via membrane Gαi subunit proteins induces MMP-9 activation either directly by GPCR ligands or indirectly in alliance with TLR receptors, this GPCR-signaling being involved in the activation of Neu1 in alliance with MMP-9 and TLR receptors on the cell surface. Here, a novel membrane sialidase-controlling mechanism is identified that depends on ligand (LPS) binding to its TLR to induce mammalian neuraminidase-1 (Neu1) activity, to influence TLR receptor desialylation of α-2,3-sialyl residues, and subsequently to induce TLR receptor activation and the production of nitric oxide and proinflammatory cytokines in dendritic and macrophage cells.

This study model supports a prerequisite desialyation of TLR receptors caused by activated Neu1 enabling the removal of a steric hindrance to receptor association with subsequent activation of TLR receptors and cellular signaling, with this molecular organizational GPCR signaling platform being an initial processing stage for GPCR agonist-induced transactivation of TLRs and subsequent downstream NFκB signaling. This signaling paradigm is proposed to be active in the ACE 2 receptor as well, critical to viral entry into the cell.

Figure 3A:
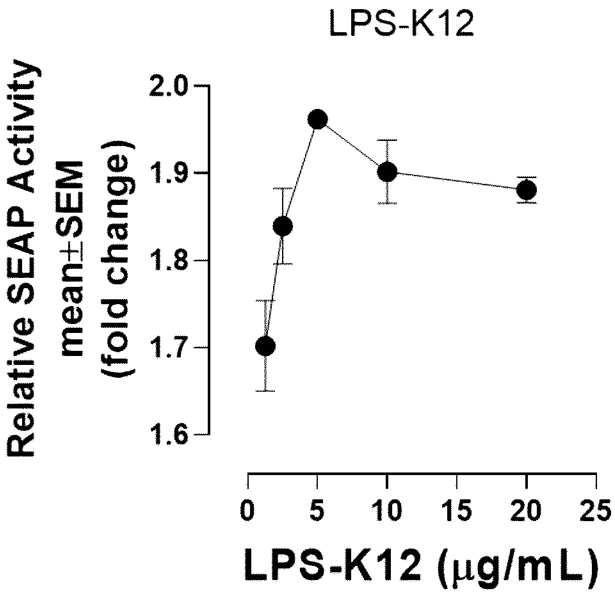
FIG. 3A shows sialidase activity in live RAW-blue macrophage cells associated with LPS K-12 at various concentrations as determined by a SEAP reporter assay per Example 2. LPS K-12 triggered increased expression of SEAP, which is reflective of nuclear factor kappa B (NF-kB) expression and downstream induction of inflammatory molecules.

In FIG. 3A, RAW-Blue™ cells were used to measure the LPS induced macrophage activation. These cells are derived from the murine RAW 264.7 macrophages with chromosomal integration of a SEAP reporter construct inducible by NF-κB and AP-1. RAW-Blue™ cells express many pattern-recognition receptors (PRRs), including toll-like receptors (TLRs), NOD-like receptors (NLRs), RIG-1-like receptors (RLRs) and C-type lectin receptors (CLRs). Upon stimulation, RAW-Blue™ cells activate NF-kB and AP-1, leading to the secretion of SEAP, which is detectable and measurable when using QUANTI-Blue™, a SEAP detection medium. The data in FIG. 3A demonstrate that LPS binding TLR induced SEAP secretion dose-dependently as a measure of NF-κB and AP-1 activation with subsequent proinflammatory cytokine activity.

Figure 3B:
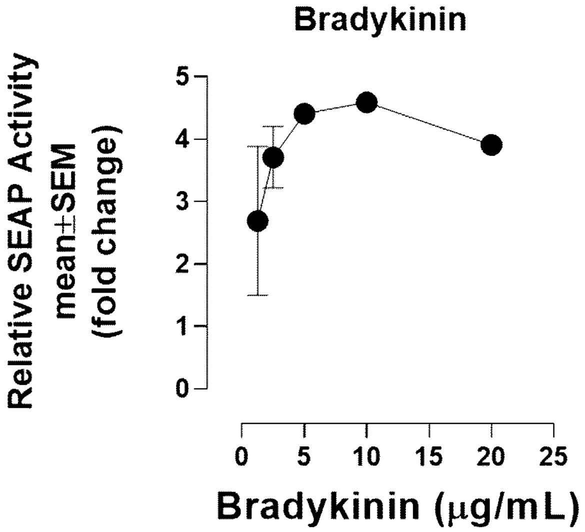
FIG. 3B shows sialidase activity in live RAW-blue macrophage cells associated with bradykinin at various concentrations as determined by a SEAP reporter assay per Example 2. Bradykinin triggered increased expression of SEAP, which is reflective of NF-kB expression and downstream induction of inflammatory molecules.
Figure 3D:
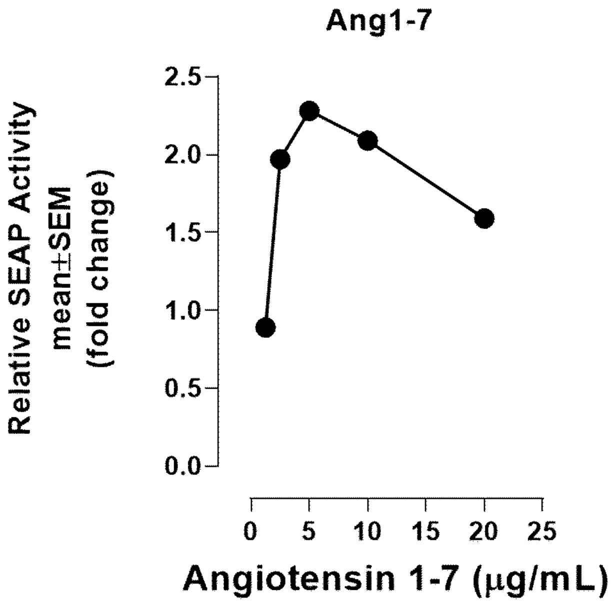
FIG. 3D shows sialidase activity in live RAW-blue macrophage cells associated with neuropeptide FF at various concentrations as determined by a SEAP reporter assay per Example 2. Neuropeptide FF triggered increased expression of SEAP, which is reflective of NF-kB expression and downstream induction of inflammatory molecules.
Figure 3D:
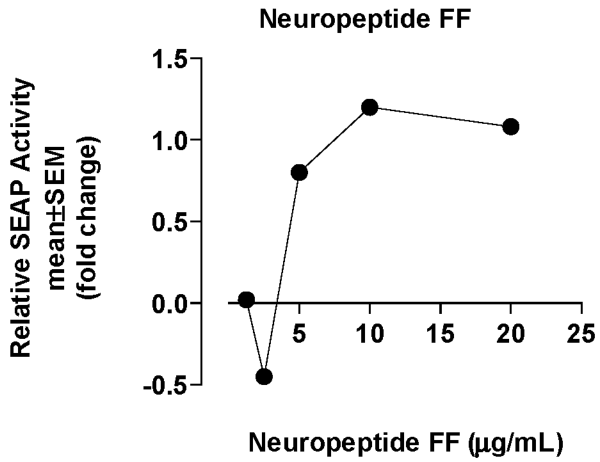
Figure 4A:
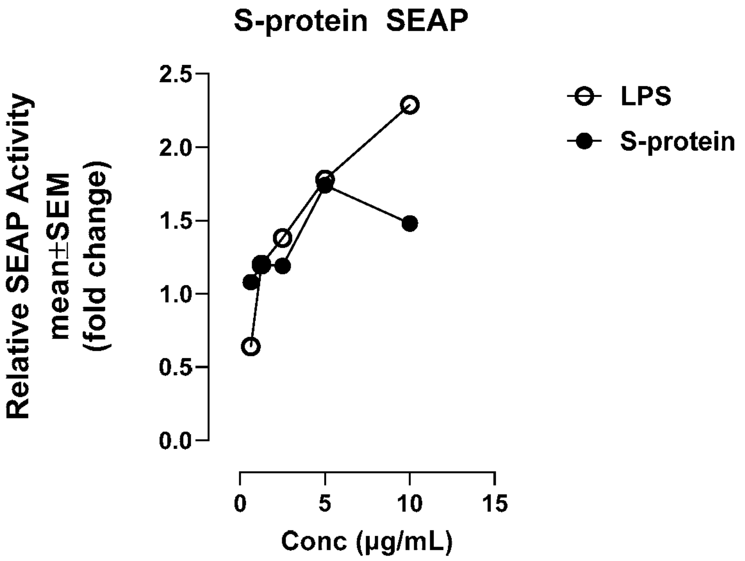
FIG. 4A shows sialidase activity in live RAW-blue macrophage cells associated with LPS and S-protein at indicated concentration as determined by a SEAP reporter assay per Example 2.
Figure 4B:
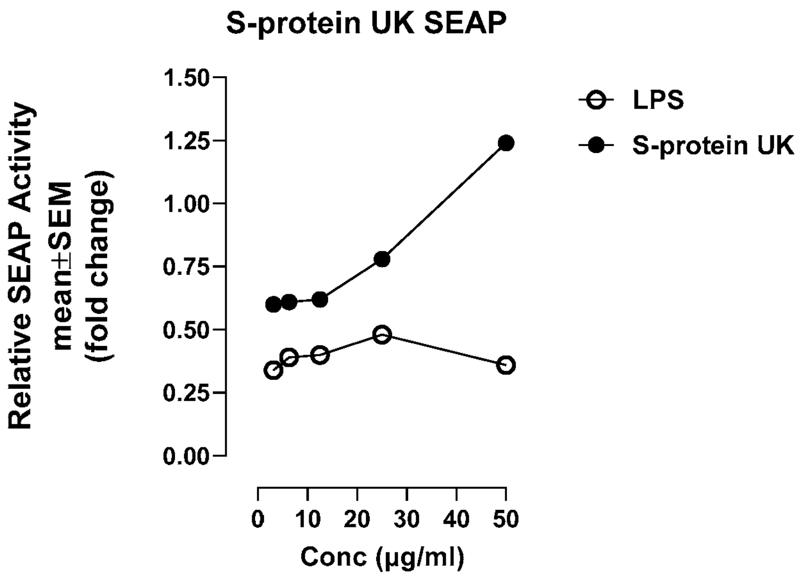
FIG. 4B shows sialidase activity in live RAW-blue macrophage cells associated with LPS and S-protein UK at indicated concentration as determined by a SEAP reporter assay per Example 2.
Figure 4C:
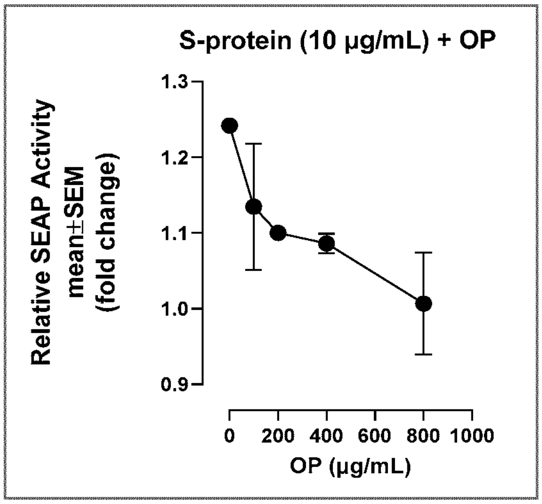
FIG. 4C shows sialidase activity in live RAW-blue macrophage cells exposed to S-protein at a concentration of 10 ug/mL and OP at indicated concentrations. OP inhibited sialidase activity in a dose dependent manner as determined by a SEAP reporter assay per Example 2.
Figure 5:
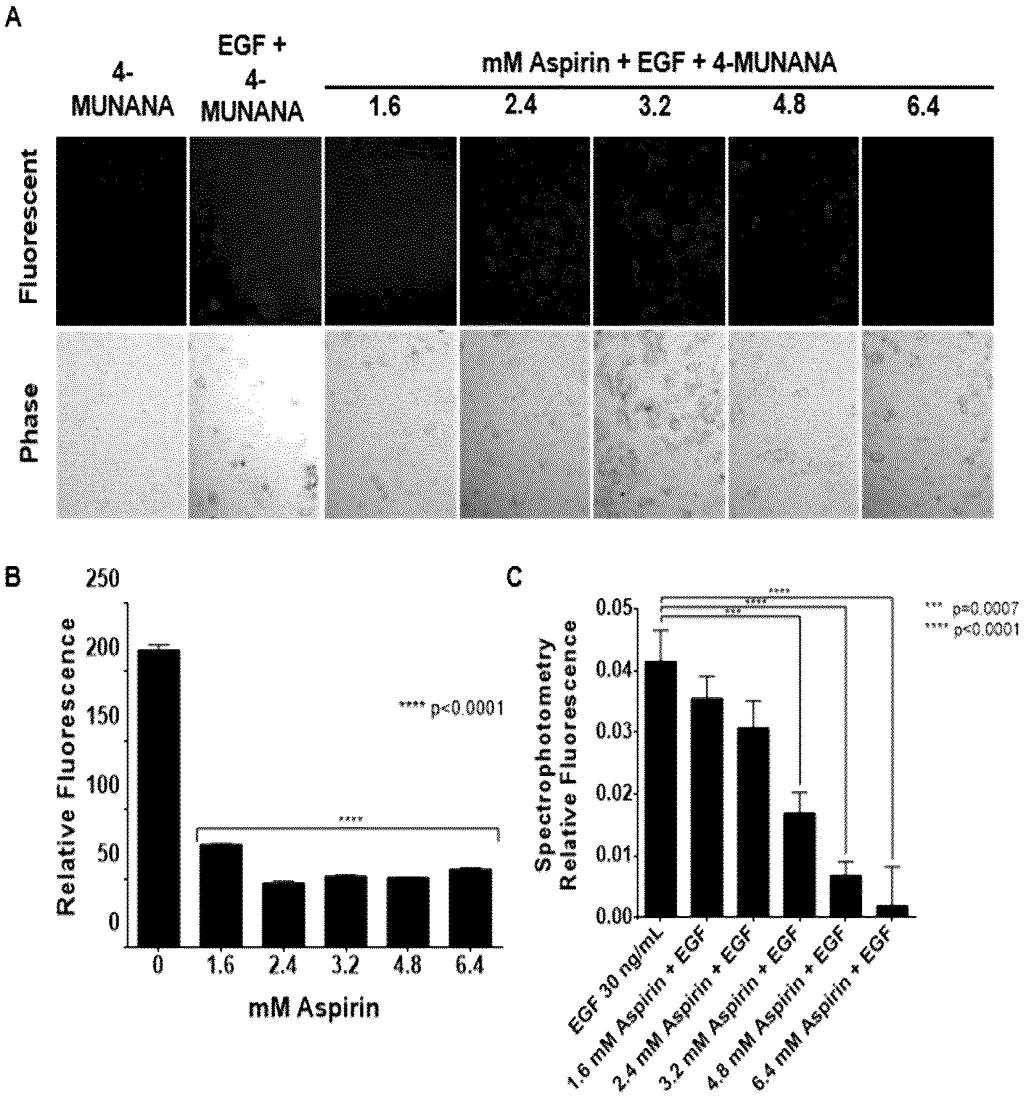
FIG. 5 shows the ability of aspirin to inhibit neuraminidase 1 in a human pancreatic cancer cell line. Live PANC-1 cells were pre-treated with increasing concentrations of aspirin (1.6 mM-6.4 mM), followed by stimulation with 30 ng/mL of EGF to initiate Neu-1 activity. 0.318 mM 4-MUNANA substrate was added to quantify Neu-1 activity. Graph shows substantial reduction in Neu-1 activity with aspirin concentrations listed.

In FIG. 3B, the data show that bradykinin dose-dependently induces SEAP secretion in RAW-Blue™ cells. When the COVID-19 virus interacts with its receptor ACE2, it triggers an abnormal response in the bradykinin pathway. Levels of angiotensin-converting enzyme, which is involved in the breakdown of bradykinin, are lower in COVID-19 patients than in healthy controls. These COVID-19 patients will develop hyper-permeable blood vessel fluid pouring out of the infected areas and into the lungs, a "Bradykinin Storm." Also, patients with COVID-19 develop dysregulated genes responsible for synthesizing hyaluronic acid, a polymer that can absorb more than 1,000 times its weight in water. Together, the bradykinin storm will cause blood vessels to leak, and the hyaluronic acid dysregulation will pour massive quantities of a gel-like substance into the alveoli. This outcome aligns with autopsy reports that detail the lungs of patients with COVID-19.

The present inventors have found that bradykinin (BR2) and angiotensin II receptor type I (AT2R) exist in a multimeric receptor complex with neuromedin B (NMBR) GPCR tethered to TLR and Neu1 in naïve (unstimulated) and stimulated macrophage cells. Here, a molecular link regulating the interaction and signaling mechanism(s) between these molecules on the cell surface uncover a biased bradykinin B2 GPCR agonist-induced TLR transactivation signaling axis, mediated by Neu1 sialidase and the modification of TLR receptor glycosylation. The biased G-protein-coupled receptor (GPCR)-signaling platform potentiates neuraminidase-1 (Neu1) and matrix metalloproteinase-9 (MMP-9) crosstalk on the cell surface that is essential for the activation of the TLR receptor.

In FIGS. 3C and D, the data show that angiotensin 1-7 (FIG. 3C) and neuropeptide FF (FIG. 3D) dose-dependently induce SEAP secretion in RAW-Blue™ cells. In several disease states, activation of the ACE/angiotensin II (Ang II)/angiotensin receptor type I (AT2R) GPCR receptor, can cause deleterious effects, including vasoconstriction, inflammation, fibrosis, cellular growth and migration and fluid retention. In addition to the ACE/Ang II/AT2R receptor axis, the renin-angiotensin system (RAS) possesses a counter-regulatory axis composed by ACE2, angiotensin-(1-7) [Ang-(1-7)] and the Mas GPCR receptor.

Ang-(1-7) is produced mainly through the action of ACE2, which has approximately 400-fold less affinity for Ang I than Ang II. Therefore, Ang II is the major substrate for Ang-(1-7) synthesis. Ang-(1-7)/MAS mediates its effects that oppose actions of Ang II/AT1. MAS GPCR can interact with other GPCRs.

MAS agonists such as neuropeptide FF, exhibit biased signaling of MAS itself. Heteromeric interactions of MAS with AT1, AT2, bradykinin B2, and endothelin B receptors have been reported. Thus, MAS GPCR can affect biased signaling differently in these receptors, thus reinforcing the idea that the potential allosteric site is different in the two receptors. We hypothesize that MAS GPCR may be affecting other GPCRs ("off-side"), by interacting with lipid-receptor interfaces or other partner receptors.

The Examples evidence a novel regulatory action of MAS involved in the GPCR biased agonist-induced TLR receptors.

GPCR and inflammatory molecules released are posited to trigger activation of a cytokine storm in COVID-19 patients by this mechanism.

What is claimed is:

1. A method of treating a coronavirus infection or suspected coronavirus infection comprising administering intravenously or via inhalation to a patient in need thereof a therapeutically effective amount of oseltamivir phosphate, wherein the oseltamivir phosphate inhibits mammalian neuraminidase-1.

2. A method of treating or preventing acute respiratory distress syndrome (ARDS) comprising administering intravenously or via inhalation to a patient in need thereof a therapeutically effective amount of oseltamivir phosphate, wherein the oseltamivir phosphate inhibits mammalian neuraminidase-1.

3. The method of claim 2, wherein the patient is diagnosed with a coronavirus infection.

4. The method of claim 2, wherein the patient is diagnosed with sepsis.

5. The method of claim 1, wherein the coronavirus is COVID-19.

6. The method of claim 1, wherein the patient has atelectasis and/or hypoxemia.

7. The method of claim 1, wherein the patient has one or more symptoms of respiratory compromise selected from shortness of breath, rapid breathing, and bluish skin coloration.

8. The method of claim 7, wherein the method ameliorates or alleviates one or more of symptoms selected from shortness of breath, rapid breathing, and bluish skin coloration.

9. The method of claim 1, comprising administering oseltamivir phosphate at a daily dose of between 100 mg and 1000 mg intravenuously or via inhalation.

10. The method of claim 1 further comprising administering a therapeutically effective amount of aspirin to the patient.

11. The method of claim 10, wherein the aspirin is administered orally concurrently with the oseltamivir phosphate administered intravenously or via inhalation.

12. The method of claim 10, wherein the aspirin is administered orally at a daily dose of between 100 mg and 1000 mg.

13. The method of claim 1 comprising:

administering to the patient a bolus dose of between 100 mg and 1000 mg of oseltamivir phosphate by intravenous injection or inhalation;

subsequently administering an additional dose of between 100 mg and 1000 mg of oseltamivir phosphate over 24 hours by continuous infusion; and orally administering to the patient aspirin at a dose of between 100 mg and 1000 mg.

14. The method of claim 2, further comprising concurrently orally administering a therapeutically effective amount of aspirin to the patient.

15. The method of claim 1, comprising administering intravenously an effective amount of oseltamivir phosphate.

16. The method of claim 2, wherein administering the therapeutically effective amount of oseltamivir phosphate decreases the plasma/serum level of one or more of IL-6, TNFα, G-CSF, MCP-1, and MIP-1a pro-inflammatory cytokines by ≥5%, ≥10% or ≥25% within 24 hours.

17. The method of claim 1, wherein administering the therapeutically effective amount of oseltamivir phosphate decreases viral load by ≥5%, ≥10% or ≥25% within 24 hours.

* * * * *